United States Patent
Brundage et al.

(10) Patent No.: US 10,429,629 B1
(45) Date of Patent: Oct. 1, 2019

(54) IMAGING AND SIDE-SCATTER PHOTON DETECTION USING A SINGLE IMMERSION OBJECTIVE

(71) Applicant: Verily Life Sciences LLC, Mountain View, CA (US)

(72) Inventors: Michael Brundage, Los Altos, CA (US); Supriyo Sinha, Menlo Park, CA (US); Andrew Homyk, Belmont, CA (US); Saurabh Vyawahare, Mountain View, CA (US)

(73) Assignee: Veily Life Sciences LLC, Mountain View, CA (US)

( * ) Notice: Subject to any disclaimer, the term of this patent is extended or adjusted under 35 U.S.C. 154(b) by 72 days.

(21) Appl. No.: 15/490,807

(22) Filed: Apr. 18, 2017

(51) Int. Cl.
*G02B 21/33* (2006.01)
*G02B 21/26* (2006.01)
*G02B 21/06* (2006.01)
*G02B 21/36* (2006.01)
*G02B 27/14* (2006.01)
*G01N 15/14* (2006.01)

(52) U.S. Cl.
CPC ......... *G02B 21/33* (2013.01); *G01N 15/1434* (2013.01); *G01N 15/1468* (2013.01); *G02B 21/06* (2013.01); *G02B 21/26* (2013.01); *G02B 21/365* (2013.01); *G02B 27/141* (2013.01)

(58) Field of Classification Search
CPC ........ G02B 21/33; G02B 21/06; G02B 21/26; G02B 27/141; G01N 15/1434; G01N 15/1468
See application file for complete search history.

(56) References Cited

U.S. PATENT DOCUMENTS 7,311,881 B2 * 12/2007 Takenaka .......... B01L 3/502723
422/503
7,659,980 B1 * 2/2010 Mitchell ............ G01N 21/4785
356/338

(Continued)

OTHER PUBLICATIONS

Introduction to flow cytometry, Abcam.com, 8 pages.
(Continued)

*Primary Examiner* — Thai Q Tran
*Assistant Examiner* — Jose M Mesa
(74) *Attorney, Agent, or Firm* — McDonnell Boehnen Hulbert & Berghoff LLP

(57) ABSTRACT

Methods and systems are provided to facilitate simultaneous high-resolution microscopic imaging of cells and detection of side-scattered light from such cells using an immersion objective. A container maintains a volume of an immersion oil or other immersion fluid in contact with the immersion objective and with a stage that contains a sample of the cells. The container also includes a window through which the cells can be illuminated off-axis to generate side-scattered light. The side-scattered light can then be detected through the immersion objective. The container maintains the immersion fluid in contact with an internal surface of the window to control the geometry of the optical interface between the off-axis illumination source and the immersion fluid. These systems permit high-throughput identification and imaging of cells for biological research, improvement of side-scatter cell classifiers, improved high-throughput cell sorting, and other applications.

17 Claims, 5 Drawing Sheets

(56) References Cited

U.S. PATENT DOCUMENTS

| | | | | |
|---|---|---|---|---|
| 8,179,597 | B2* | 5/2012 | Namba | G01N 21/6458 |
| | | | | 359/383 |
| 9,658,057 | B2* | 5/2017 | Leconte | G01N 21/90 |
| 9,835,552 | B2* | 12/2017 | Wagner | G01N 15/14 |
| 2009/0273774 | A1 | 11/2009 | Sieracki et al. | |

OTHER PUBLICATIONS

Hall et al., "Multispectral High Content Cellular Analysis Using a Flow Based Imaging Cytometer", Amnis.
Choi et al., "Three-Dimensional Image Cytometer Based on Widefield Structured Light Microscopy and High-Speed Remote Depth Scanning", 2015, pp. 1-14.
Steen, "Light Scattering Measurement in an Arc Lamp-Based Flow Cytometer", Cytometry 11, 1990, pp. 223-230.
Steen, "Flow cytometer for measurement of the light scattering of viral and other submicroscopic particles", Jan. 22, 2004, 13 pages.
Introduction to Flow Cytometry: A Learning Guide, Dec. 2002.
Lindmo et al., "Characteristics of a Simple, High-Resolution Flow Cytometer Based on a New Flow Configuration", Biophysical Journal, vol. 28, 1979.

\* cited by examiner

IMAGING AND SIDE-SCATTER PHOTON DETECTION USING A SINGLE IMMERSION OBJECTIVE

BACKGROUND

Unless otherwise indicated herein, the materials described in this section are not prior art to the claims in this application and are not admitted to be prior art by inclusion in this section.

A variety of methods exist to optically interrogate biological tissues or other materials at the micro-scale (i.e., at scales at or smaller than a few micrometers). Such methods can include imaging techniques used to generate images of a sample at the micro-scale. Such techniques can include a variety of methods of optical microscopy for receiving, focusing, or otherwise conditioning image light received from a sample. In some examples, an objective of an optical microscope or other imaging instrument could be configured to be in contact with an oil or other imaging fluid to facilitate higher-resolution imaging.

Such imaging techniques can also include a variety of methods for illuminating a sample, e.g., to elicit fluorescence, to bleach a fluorophore, to illuminate the sample at a particular location and/or wavelength (e.g., using a method of confocal microscopy), to provide structured illumination, or some other method for illumination.

Optically interrogating biological tissues or other materials can also include illuminating the tissues or materials and detecting a property of the interaction between the illumination and the tissues or materials. This could include detecting a property of light transmitted through, scattered by, refracted by, or otherwise modified by interaction with the tissues or materials. Such detected properties could include absorption spectra, transmission spectra, scattering spectra, or other properties. In some examples, a dimension, roughness, identity, or other information about the biological tissues (e.g., about biological cells) or other materials could be determined from the detected optical properties.

SUMMARY

Some embodiments of the present disclosure provide a system including: (i) a stage; (ii) an immersion objective; (iii) a container disposed on the stage; (iv) a light source; (v) a light sensor; and (vi) an image sensor. The container includes an optical window and is shaped to hold a volume of an immersion fluid such that the immersion fluid is in contact with the immersion objective, the stage, and an internal surface of the optical window. The light source is optically coupled to a first target region located on or within the stage via the optical window of the container. The light sensor is optically coupled to the first target region via the immersion objective and receives scattered light from the first target region. The scattered light received by the light sensor includes light from the light source that has been scattered by one or more scatterers present in the first target region. The image sensor is optically coupled to a second target region located on or within the stage via the immersion objective and receives in-focus light from the second target region.

Some embodiments of the present disclosure provide a method including: (i) illuminating, using a light source, a first target region located on or within a stage; (ii) detecting, using a light sensor, an intensity of scattered light from the first target region, wherein the scattered light includes light from the light source that has been scattered by one or more scatterers present in the first target region; and (iii) generating, using an image sensor, an image of a second target region on or within the stage. A container is disposed on the stage. The container includes an optical window and contains a volume of immersion fluid such that the contained volume of immersion fluid is in contact with an immersion objective, the stage, and an internal surface of the optical window. Illuminating the first target region includes using the light source to provide illumination to the first target region via the optical window of the container. The light sensor receives the scattered light from the first target region via the immersion objective. The image sensor receives, via the immersion objective, in-focus light from the second target region.

These as well as other aspects, advantages, and alternatives, will become apparent to those of ordinary skill in the art by reading the following detailed description, with reference where appropriate to the accompanying drawings.

DETAILED DESCRIPTION

Figure 1:
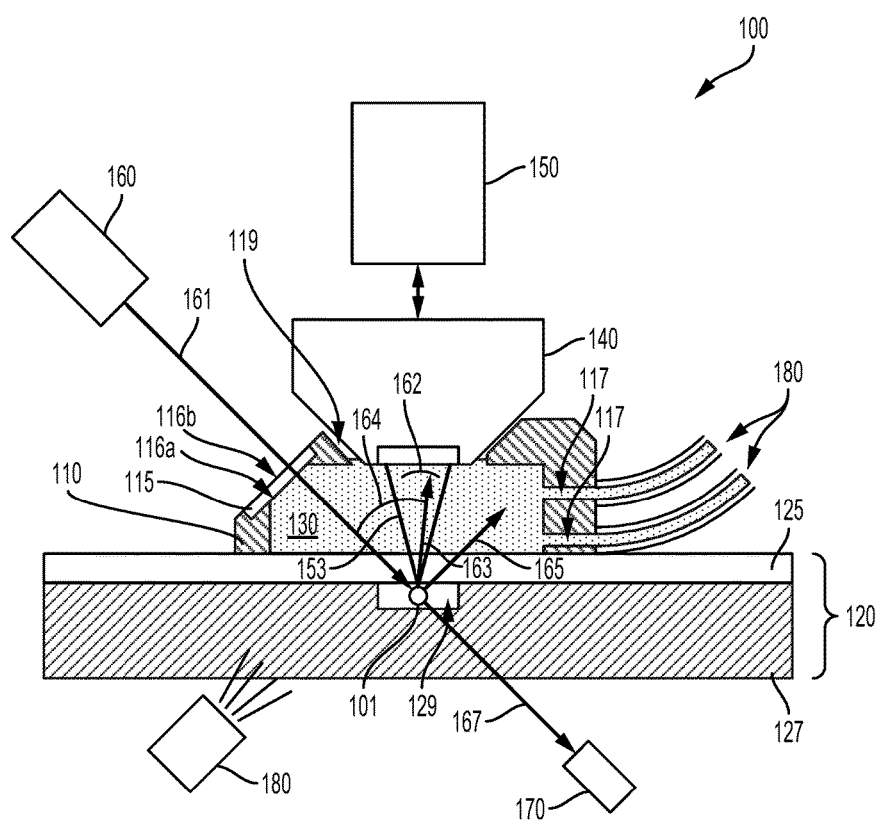
FIG. 1 illustrates an example imaging apparatus.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with samples of tissue extracted from a human or animal body, it is contemplated that the disclosed methods, systems and devices may be used in any environment where imaging, side-scatter optical characterization, sorting, and/or other processes related to other substances (e.g., other micro- or nano-scale cells, particles, or other objects suspended in a flowing carrier fluid) are desired.

I. Overview

Cells, particles, or other objects could scatter, refract, diffract, absorb, transmit, or otherwise interact with light in a manner that is related to an identity, a diameter or size, a surface texture or roughness, a characteristic dimension of a surface texture, a composition, a density, an absorption spectrum, or other properties of the objects. For example, an amount of light scattered, by a cell, at one or more angles relative to an angle of light incident on the cell could be related to an identity of the cell (e.g., to whether the cell is a red blood cell, a neutrophil, a leukocyte). Thus, the identity or other information about a population of cells, particles, or other scatterers could be determined by illuminating such scatterers and detecting an intensity or other property of light scattered by and/or transmitted through the scatterers. The scatterers could be disposed within a microfluidic channel to facilitate such illumination and/or detection (e.g., a particular portion of a channel of a microfluidic system could be illuminated, and light scattered therefrom could be detected) or to facilitate some other application (e.g., physical sorting of cells into one or more location according to, e.g., the cell type, identity, or other determined or detected characteristics of the cells).

In some applications, it could be advantageous to image such cells, particles, or other scatterers, e.g., using a microscope. For example, an identification and/or sorting of a cell could be improved by performing such operations based on both a detected intensity of light scattered by the cell and a microscopic image of the cell. To increase the resolution or otherwise improve the imaging or other optical characterization of such objects, an immersion fluid could be disposed between, and in contact with, such an object (or a stage, slide, channel, or other apparatus containing the object) and an objective of an optical system used to receive light from (e.g., to image) the object. An index of refraction of such a fluid and/or an index of refraction of a lens or other elements of such an objective (e.g., of an immersion objective configured to be immersed in or otherwise in contact with such a fluid) could be matched or otherwise specified to facilitate such imaging. Additionally or alternatively, such an immersion objective could be used to facilitate an improvement in the detection of the intensity or other properties of light scattered by the scatterers (e.g., to increase a collection efficiency of detection the side-scattered light). In such examples, the immersion objective could be used to receive the side-scattered light without imaging the scatterers (e.g., by receiving image light from the scatterers via the immersion objective and directing the received image light to an image sensor).

However, the proximity of such an immersion objective to cells or other scatterers to be imaged could impede the illumination of such scatterers and/or could impede the detection of light scattered therefrom. In some examples, the scattered light could be received, by a photomultiplier or other light sensor, from a location of the scatterers via an immersion objective that is optically coupled with the scatterers via a volume of immersion fluid. For example, the scatterers could be located on or within a stage (e.g., within a channel or other microfluidic feature of the stage), and the stage could be optically coupled to the immersion objective via a volume of immersion fluid. The scatterers could be illuminated by light that is emitted from a light source and then propagates through the volume of immersion fluid to the scatterers (e.g., to the stage on or within which the scatterers are located). Such a light source could include a laser or other means for generating a beam of illumination. The use of such an immersion objective could increase the collection efficiency of detection of light side-scattered by the scatterers or could provide some other benefit.

It could be advantageous to control the optical coupling of such a light source to scatterers illuminated thereby. A curvature, an angle relative to the light source, and/or a location of a surface of a volume of the immersion fluid (e.g., of a drop of the immersion fluid) that is disposed between and in contact with the immersion objective and a stage containing the scatterers could affect the optical coupling between the light source and the scatterers, so control of such properties could facilitate illumination of the scatterers.

To facilitate illumination of the scatterers and/or detection of light scattered therefrom, a container could be disposed on a stage or within which the scatterers are disposed. Such a container could hold a volume of immersion fluid such that the immersion fluid is in contact with the immersion objective and with the stage. The container could additionally include an optical window, an internal surface of which is also in contact with the immersion fluid held within the container. The light source could be optically coupled to the scatterers on or within the stage (e.g., to a target region within the stage) via the optical window (e.g., a beam of illumination from the light source could be transmitted from the light source, through the window and the immersion fluid, to illuminate a target region on or within the stage). The optical coupling between the light source and the scatterers, via the window, immersion fluid, and/or stage, could remain substantially unchanged despite changes in the amount of the immersion fluid that is held within the container (e.g., due to evaporation and/or replenishment of the fluid), changes in the location of the immersion objective relative to the stage (e.g., due to movement of the immersion objective to image different regions of the stage), or due to some other processes.

Other configurations, modes and methods of operation, and other embodiments are anticipated. Systems and/or methods described herein could include additional microscopic or other imaging modalities and/or optical systems or elements to improve the imaging and/or identification of cells or other features or contents of a biological sample or other material sample as described herein. A system as described herein could include multiple light sources, multiple objectives, multiple stages, multiple optical windows, multiple containers for holding immersion fluid, multiple microfluidic channels, multiple light sensors (e.g., cameras, spectrometers, photomultipliers), multiple dichroic mirrors, gratings, prisms, filters, or other optical elements, and/or additional components according to an application.

Systems and methods described herein could be used to identify and/or determine properties of cells, particles, or other microscopic features or elements in a variety of different environments, e.g., in vitro biological environments, samples of geological or other samples suspended in a carrier fluid, or some other environments and/or samples. Further, systems and methods as described herein could be configured or operated according to and/or in combination with a variety of different microscopic or other imaging techniques, e.g., stimulated emission depletion, ground state depletion, saturated structured illumination microscopy, 4pi imaging, photobleaching, confocal microscopy, hyperspectral imaging, or other methods or techniques.

It should be understood that the above embodiments, and other embodiments described herein, are provided for explanatory purposes, and are not intended to be limiting.

II. Example Imaging Apparatus

It could be advantageous in a variety of applications to be able to use an immersion objective to detect light scattered from a target region (e.g., laser light scattered from a region that may contain cells, particles, or other scatterers). For example, the use of such an objective to receive such scattered light could increase a collection efficiency of detection of the side-scattered light. Additionally or alternatively, such use could facilitate the detection of the scattered light while also permitting the contents of such a region to be imaged (e.g., at a high resolution facilitated by use of the immersion objective and an immersion fluid). For example, it could be advantageous to sort cells, engineered nanoparticles, or other small light-scattering objects disposed, e.g., in a flowing carrier fluid. Such sorting could be based on images of the light-scattering objects and information about the intensity of light scattered by the light-scattering objects in one or more directions. In another example, an algorithm for sorting cells or other light-scattering objects based on the light scattered by the cells could be improved using such information. This could include generating images of the cells, identifying the cells (e.g., determining a type, subtype, size, or other information about the cells), and comparing the identification of the cells to one or more detected properties (e.g., a time-varying intensity) of light scattered by the identified cells. Additional or alternative applications could be improved by access to such information and/or imaging apparatus.

In order to generate high-resolution microscopic images of such a target region, an oil, aqueous solution, high-index fluid, or other microscopy immersion fluid could be disposed between a microscope immersion objective (e.g., an immersion objective configured to be immersed in or otherwise placed into contact with such a fluid) and a stage or other sample-holding apparatus that includes the target region. A container disposed on the stage could include an optical window and could hold a volume of the immersion fluid in contact with the immersion objective (e.g., with a lens or other external optical element of the immersion objective), an internal surface of the optical window, and the stage. The light source could then emit light to illuminate the target region via the optical window. A portion of the emitted light could be scattered by scatterers (e.g., cells) in the target region and detected (e.g., using a photomultiplier or other light-sensitive elements) via the immersion objective. The immersion objective could also receive light used to image scatterers in the target region or in some other region on or within the stage. This could include providing light from the stage to an image sensor via the immersion objective such that the light arrives at the image sensor in focus.

Such a configuration of elements permits the light source and/or some additional components (e.g., additional light sources) to be optically coupled to the target region in the stage (e.g., the target region that may contain one or more cells, engineered particles, or other scatterers) via the optical window. By containing the immersion fluid within such a container in contact with the stage and the internal surface of the optical window, the optical coupling between the light source and/or additional components and the target region within the stage may be controlled. For example, the optical coupling between the light source and the target region may be substantially unchanged despite evaporation or replenishment of the immersion fluid, relative motion between the immersion objective and the stage, or some other processes or factors.

FIG. 1 illustrates in cross-section elements of an example imaging system 100 configured to optically interrogate one or more scatterers 101 (e.g., cells, engineered particles, or other scattering objects) present in a first target region on or within a stage 120. The system 100 includes a light source 160, an immersion objective 140, a container 110 disposed on the stage 120, and an optical system 150 that is optically coupled to the immersion objective 140. The optical system 150 includes a light sensor configured to detect an intensity of light scattered by the one or more scatterers 101 and an image sensor configured to image in-focus light from the first target region or from some other location on or within the stage 120. The container 110 includes an optical window 115 and holds a volume of an immersion fluid 130 (e.g., a high-refractive-index oil, saline, or other fluid) in contact with an internal surface 116a of the optical window 115, the stage 120, and the immersion objective 140.

As shown in FIG. 1, the one or more scatterers 101 are disposed within a channel 129 formed in the stage 120. The first target region is illuminated by the light source 160 and encompasses at least a portion of the channel 129. The one or more scatterers 101 could include cells, e.g., cells extracted from a human body by a blood draw, a biopsy, or some other process(es). Additionally or alternatively, the one or more scatterers 101 could include some other particles or other light-scattering objects. For example, the one or more scatterers 101 could include particles of an optical and/or magnetic contrast agent, particles configured to collect an analyte of interest when disposed within a body or other environment of interest, magnetic nanoparticles, or other engineered or natural particles of interest.

The one or more scatterers 101 could be disposed within a carrier fluid (e.g., blood plasma, a saline solution, an aqueous solution, an oil) to facilitate transport of the one or more scatterers 101 through the channel 129, e.g., into and out of the first target region. Such transport through a first target region could facilitate imaging, side-scatter optical characterization or identification, sorting into one or more locations, performing additional characterization of the one or more scatterers (e.g., by passage between electrodes to facilitate electrical impedance detection), or some other applications. The stage 120 could include multiple such channels and/or the channel 129 could be part of a microfluidic circuit (e.g., for sorting cells, for sequentially side-scatter characterizing and imaging cells). The channel 129 could be in fluid communication with means for sorting cells or other scatterers (e.g., engineered particles, magnetic nanoparticles) into one or more locations (e.g., into respective different locations corresponding to different types of scatterers, different ranges of sizes of scatterers, different ranges of some other detected property of the scatterers).

As shown in FIG. 1, the light source 160 is optically coupled to the first target region via the optical window 115 of the container 110. The light source 160 can operate to emit light 161 that illuminates the one or more scatterers 101. The one or more scatterers 101 then scatter an amount of the light 161 from the light source 160 (shown as scattered light 163 and 165). The one or more scatterers 101 also forward scatter and/or transmit an amount of the light 161 from the light source 160 (shown as transmitted light 167). The light sensor in the optical system 150 is optically coupled to the first target region via the immersion objective 140 and receives scattered light 163 from the first target region.

The scattered light received by the light sensor, via the immersion objective 140, could include light scattered by the one or more scatterers 101 within a specified range of angles, e.g., within the illustrated range of angles 162. Such a range of angles could be specified relative to a direction of the light 160 (e.g., of a beam of light) emitted by the light source 160 to illuminate the first target region. For example, the specified range of angles could be between 85 and 95 degrees, between 88 and 92 degrees, between 80 and 90 degrees, between 83 and 97 degrees, between 88 and 90 degrees, between 88.5 and 89.5 degrees, or between some other specified range of angles relative to such a beam of illumination. Such a range of angles could include an angle between such a beam of illumination and an optical axis of the immersion objective, e.g., the illustrated angle 164 between the light 161 from the light source 160 and the scattered light 163. For example, light scattered at 91 degrees, 91.5 degrees, 90 degrees, 89.5 degrees, 89 degrees, 88.5 degrees, or 88 degrees relative to a beam of illumination could be received by the light sensor via the immersion objective 140.

The image sensor in the optical system 150 is optically coupled to a second target region on or within the stage such that the image sensor receives in focus light 153 from the second target region. As shown in FIG. 1, the second target region could partially or fully overlap with the first target region, e.g., such that the image sensor can generate images of the one or more scatterers 101 that are scattering the scattered light received by the light sensor. Additionally or alternatively, the second target region could be non-overlapping with the first target region. For example, the second target region could include a portion of the channel 129 that is downstream of the portion of the channel 129 that is within the first target region. In such an example, a flow of carrier fluid could be provided in the channel 129 such that the one or more scatterers 101 that scattered the scattered light 163 when present in the first target region could flow downstream through the channel 129 to the second target region and imaged by the image sensor. In such examples, the imaging of the scatterers, using the image sensor, could be performed in response to identifying the scatterers based on an intensity or other detected property of the light scattered by the scatterers and received by the light sensor while the scatterers were in the first target location. This operation could facilitate the imaging of the scatterers (e.g., by setting an exposure timing, exposure duration, or other properties of the imaging based on the detected identity) or could facilitate some other application.

The in-focus light 153 could be emitted from the second target area in response to illumination of the second target area. In some examples, the illumination could be provided by the light source 160 (e.g., the light source 160 could provide light that is received by the image sensor and light that is scattered and received by the light sensor). Additionally or alternatively, the second target area could be illuminated by some other light source. For example, the imaging system 100 could include a further light source 180 configured to illuminate the second target area and/or the first target area. In another example, the optical system 150 could include one or more light sources configured to illuminate the second target area via the immersion objective.

Note that the system 100 and elements thereof shown in FIG. 1 are intended as a non-limiting example of systems and methods as described elsewhere herein for illuminating one or more scatterers present in a first target region, detecting a property of light responsively scattered by the scatterers via an immersion objective, and imaging a second target region (that may partially overlap with the first target region) via the immersion objective. Such systems and methods could be provided to facilitate identification and/or sorting of cells or other scatterers present in the first and/or second target regions, to improve an algorithm for identifying cells or other scatterers based only on detected side-scattered light, to characterize or investigate cells or other scatterers based on optical properties (e.g., images, a degree or property of optical scattering) of the scatterers, or some other application. Imaging systems could include more or fewer elements, and could image one or more target regions and/or one or more scatterers according to similar or different methods. Illumination could be delivered to first and/or second target regions and light received from the target in additional or alternative ways and using differently configured elements (e.g., different optics). In some examples, an immersion objective could be used as described herein to increase a collection efficiency of detection of side-scattered light from scatterers in a target region or to provide some other benefit without using the immersion objective to image scatterers or other objects of interest (e.g., such a system could lack an image sensor).

The light source 160 could include a variety of light-emitting elements configured to produce illumination 161 having one or more specified properties (e.g., specified wavelength(s)). The illumination 161 could be coherent (e.g., laser light) or could be non-coherent (e.g., a collimated beam of light from an incandescent light source, an arc lamp, or some other monochromatic or wideband light emitter). This could include lasers, light-emitting diodes (LEDs), or other substantially monochromatic light sources. Additionally or alternatively, the light source 160 could include a light emitting element that emits light across a wider range of wavelengths (e.g., an arc lamp). In some examples, this non-monochromatic light could be emitted through one or more filters (e.g., filters including one or more Bragg reflectors, prisms, diffraction gratings, slit apertures, monochromators) configured to only allow the transmission of light within a narrow range of wavelengths. In some examples, the light source 160 could be configured to emit light at a specified wavelength or having some other specified property to excite a fluorophore of one or more scatterers present in the stage 120, to selectively scatter from a particular type, size, or other specified population of scatterers, or to otherwise selectively interact with one or more scatterers present in the stage 120.

In some examples, the light source 160 could include a gimbal, one or more actuated mirrors, a servomotor, or some other actuators to facilitate control of the location and/or orientation of the light source 160 and/or to control a location, orientation, beam width, coherence, wavelength, or other properties of the illumination 161 emitted from the light source 160. For example, the light source 160 could be configured to emit a beam of illumination (e.g., the light source 160 could include a laser, collimator, or other optical elements) to illuminate the first target region via the optical window 115. In such an example, the light source could additionally be configured to control at least one of a location or an orientation of the emitted beam of illumination. Such control could be provided to facilitate control or adjustment of the location of the first target region relative to the immersion objective 140 (e.g., to cause the first and second target regions to overlap to a greater or lesser degree), to the stage 120 (e.g., to cause the first target region to encompass the channel 129 or to cause the first target region to encompass an alternative channel or other feature or element within the stage 120), or to some other element of the imaging system 100 and or to a sample contained therein.

Additionally or alternatively, the stage 120 and/or immersion objective 140 could be movable relative to each other. In such examples, the container 110 could be shaped to permit such relative motion. For example, the container 110 could include a port 119 or other formed feature having a size greater than a size of a corresponding portion of the immersion objective 140 to permit the corresponding portion of the immersion objective 140 to move, relative to the stage and/or container 110, by a specified amount without coming into contact with the container 110. Actuation of the stage 120 and/or immersion objective 140 could include one or more piezo elements, servo motors, linear actuators, galvanometers, or other actuators configured to control the location of the immersion objective 140 and/or the stage 120 (and the container 110 mounted on the stage 120) relative to each other and/or to other elements of the imaging system 100.

As shown in FIG. 1, the one or more scatterers 101 could be contained within a channel 129 or other microfluidic feature or elements on or within the stage 120. In some examples, a stage of an imaging system as described herein could include multiple different components. In one example, the stage 120 includes a microfluidic layer 127 (that includes the channel 129) and a transparent layer 125. The transparent layer 125 could include a layer of glass, polydimethylsiloxane, poly(methyl methacrylate), cyclic olefin copolymer, or of some other transparent material to, e.g., facilitate optical coupling between the one or more scatterers 101 and the light source 160, optical window 115, and/or immersion objective 140. The transparent layer 125 could be polished to reduce scattering, diffraction, and/or absorption of light transmitted through the transparent layer 125. The microfluidic layer 127 could be transparent (e.g., could be composed of a transparent material) or could include transparent portions (e.g., windows, channels), e.g., to facilitate optical interrogation of scatterers or other samples on or within the microfluidic layer 127. The microfluidic layer 127 could include additional channels or other microfluidic features or elements, e.g., to facilitate sorting of the one or more scatterers 101 into one or more locations (e.g., according to determined identities of the one or more scatterers 101), to facilitate sequential interrogation of the one or more scatterers as the travel in a flow of a carrier fluid (e.g., sequential imaging, side-scatter optical assessment, electrical impedance assessment, fluorescence assessment, or some other measurement), or to facilitate some other application.

In some examples, the microfluidic layer 127 could be removably mounted to the transparent layer 125 (e.g., to a glass layer 125). This could include the transparent layer 125, the microfluidic layer 127, and/or some other element of the imaging system 100 having clips, mounting features, rails, screws, pins, alignment features, or other means for removably mounting the microfluidic layer 127 to the transparent layer 125 and/or for removing the microfluidic layer 127 from the transparent layer 125. The microfluidic layer 127 could be removably mounted to the transparent layer 125 to facilitate replacement of the microfluidic layer 127 after use, to facilitate use of the imaging system 100 with a variety of different types or configurations of microfluidic layer 127, to facilitate cleaning, polishing, or other processes involving the microfluidic layer 127 and/or the transparent layer 125, or to facilitate some other application.

The container 110 could have a shape, optical properties, or other properties specified to facilitate imaging and/or side-scatter interrogation of the one or more scatterers 101 or to facilitate some other application. For example, the optical window 115 could have one or more optical properties to facilitate illumination of the one or more scatterers 101, e.g., to reduce reflection of the illumination 161 at interfaces between the window 115 and the immersion fluid 130 and/or air. The optical window 115 could include an anti-reflective coating on an external surface 116b of the window 115 and/or on the internal surface 116a of the window 115. Additionally or alternatively, the optical window 115 could comprise a material (e.g., a glass) having a refractive index that matches a refractive index of the immersion fluid 130. The container 110 could include additional windows or other features (e.g., to facilitate illumination of the first target region from different angles and/or by different light sources, to facilitate detection of additional light 165 scattered from the one or more scatterers 101).

In some examples, the container 110 could include one or more channels to facilitate addition and/or removal of the immersion fluid 130 held by the container 110. As shown in FIG. 1, the container 110 includes channels 117. The channels 117 are connected, via respective tubes 180, to a pump, a reservoir of immersion fluid, a filter, or other means for adding additional immersion fluid 130 to the amount held by the container 110, removing immersion fluid 130 from the container, or for performing some other process. Such channel(s) or other means could be provided to compensate for the evaporation of the immersion fluid 130 (e.g., by adding additional immersion fluid), to compensate for changes over time in the optical properties of the immersion fluid 130, to facilitate replacement of the immersion fluid 130 with a different type of immersion fluid, to facilitate cleaning of the imaging system 100 (e.g., by removing the immersion fluid 130 and rinsing the volume within the container 110 with a cleaning solution), or to facilitate some other application.

The imaging system 100 (or other example imaging and/or microscopy systems described herein) could include additional elements or components. The imaging system 100 could include one or more controllers configured to operate the light source 160, light sensor of the optical system 150, image sensor of the optical system 150, actuator(s) configured to control the location of the stage 120 or other properties of the imaging system 100, and/or other elements of the imaging system 100. The imaging system 100 could include communications devices (wireless radios, wired interfaces) configured to transmit/receive information to/from other systems (e.g., servers, other imaging devices, experimental systems, carrier fluid pumps) to enable functions and applications of the imaging system 100. For example, the imaging system 100 could include an interface configured to present images generated by the imaging system 100. The imaging system 100 could include an interface configured to present information about the imaging system 100 to a user and/or to allow the user to operate the imaging system 100.

Additionally or alternatively, the imaging system 100 (or other example imaging systems described herein) could be configured to communicate with another system (e.g., a cellphone, a tablet, a computer, a remote server) and to present a user interface using the remote system. In some examples, the imaging system 100 could be part of another system. In some examples, the imaging system 100 could include multiple light sensors, imaging sensors, light sources, or other additional components. For example, the imaging system 100 could include an additional light sensor 170 configured to detect light 167 from the light source 160 that is forward-scattered or otherwise transmitted through the one or more scatterers 101. Other configurations, operations, and applications of imaging systems as described herein are anticipated.

A container of an imaging system as described herein (e.g., 110) could be configured to be added to an existing imaging system (e.g., an immersion microscopy system) to add to that imaging system the functionality described herein. In such examples, the container could include alignment features, fiducials, clips, pins, or other features for mounting the container to one or more elements (e.g., a stage) of such an imaging system.

In some examples, an imaging system (e.g., 100) could include one or more elements configured to separate light received, via an immersion objective, that is scattered from one or more scatterers in a first target area from in-focus light received, via the immersion objective, from a second target area. For example, the in-focus light and the scattered light could differ with respect to wavelength and the imaging system could include one or more optical filters, gratings (e.g., diffraction gratings, holographic gratings), Amici prisms, prisms, chromatically dispersive elements, dichroic mirrors, Fabry-Perot filters, Bragg reflectors, or other elements to separate the in-focus light from the scattered light such that the in-focus light is received by the image sensor and the scattered light is received by the light sensor.

Figure 2:
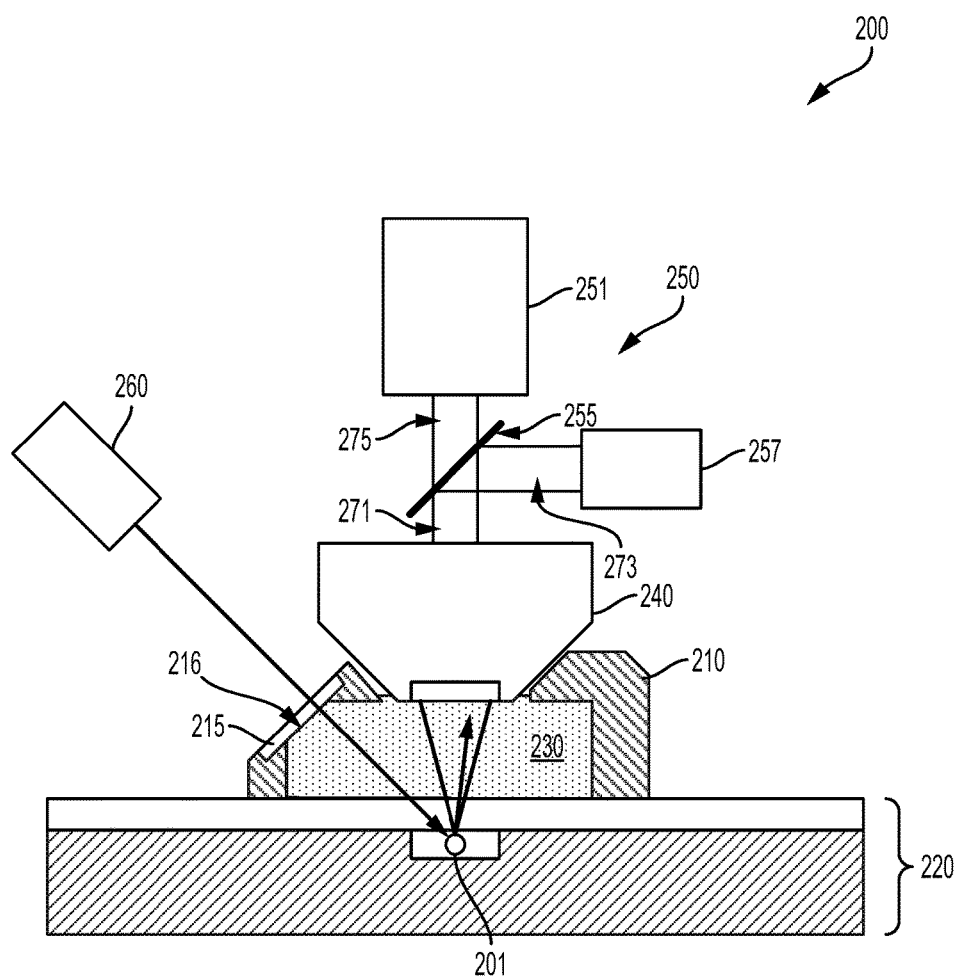
FIG. 2 illustrates an example imaging apparatus.

FIG. 2 illustrates in cross-section elements of an example imaging system 200 configured to optically interrogate one or more scatterers 201 (e.g., cells, engineered particles, or other scattering objects) present in a first target region on or within a stage 220. The system 200 includes a light source 260 (e.g., a laser), an immersion objective 240, a container 210 disposed on the stage 220, and an optical system 250 that is optically coupled to the immersion objective 240. The optical system 250 includes a light sensor 257 configured to detect an intensity of light scattered by the one or more scatterers 201, a dichroic mirror 255, and an image sensor 251 configured to image in-focus light from the first target region or from some other location on or within the stage 220. The light sensor 257 could include one or more avalanche photodiodes, photomulitiplier tubes, photodiodes, bolometers, or other light-sensitive components. The image sensor 251 could include one or more charge-coupled devices, pixel sensors, arrays of active pixel sensors, arrays of photodiodes or other light sensitive components, color filters, or other light-sensitive components or arrays of light-sensitive components. The container 210 includes an optical window 215 and holds a volume of an immersion fluid 230 (e.g., a high-refractive-index oil, saline, or other fluid) in contact with an internal surface 216 of the optical window 215, the stage 220, and the immersion objective 240.

The light source 260 emits light at a first wavelength to illuminate the one or more scatterers 201 and a portion of the emitted light is scattered by the one or more scatterers 201 and received into the immersion objective 240. The second target region could be illuminated (e.g., by a light source coupled to the second target region via the immersion objective 240, or by some other source of illumination) such that in-focus light from the second target region includes light at a second wavelength that differs from the first wavelength. This could include providing illumination to the second target region at the second wavelength. Additionally or alternatively, the second target region could include fluorophores, raman dyes, or other substances (e.g., of one or more scatterers located in the second target region) that emit light at the second wavelength in response to receiving such illumination (e.g., in response to receiving illumination at an excitation wavelength of a fluorophore. The dichroic mirror 255 receives light 271 from the immersion objective that includes the in-focus light and the scattered light. The dichroic mirror reflects light at the first wavelength and transmits light at the second wavelength such that the light sensor 257 receives the light at the first wavelength 273 via reflection from the dichroic mirror 255 and further such that the image sensor 251 receives light at the second wavelength 275 via transmission through the dichroic mirror 255.

Note that the configuration of the example imaging system 200 is intended as a non-limiting example embodiment of an imaging system that separates light received, using an immersion objective, from one or more target regions according to the wavelength of the received light. For example, in-focus light from the second target region at the second wavelength could be received by an image sensor following reflection from a dichroic mirror and scattered light at the first wavelength could be received by a light sensor following transmission through such a dichroic mirror. Additionally or alternatively, other prisms, gratings, or other chromatically dispersive elements could be used to separate light received via an immersion objective according to wavelength, e.g., such that multiple different light sensors could be operated to receive, and the detect the intensity of, light scattered by one or more scatterers at respective multiple different wavelengths.

An imaging system and/or imaging methods described herein could facilitate the identification of, imaging of, sorting of, or other processes relating to cells, engineered particles, or other scatterers. To facilitate such applications, the scatterers could be disposed within blood, saline, or some other carrier fluid to facilitate transport of the scatterers through one or more channels or other microfluidic elements or features. An imaging system could then illuminate, and receive light scattered from, scatterers located within a portion of such a channel. The channel could be in fluid communication with further channels, electrodes, cuvettes or other storage means, cell or particle sorting means, cell manipulation means (e.g., lasers), or other apparatus such that flow of the carrier fluid transports the cells or other scatterers between the first target region and such other apparatus and/or other regions within the imaging apparatus.

Figure 3A:
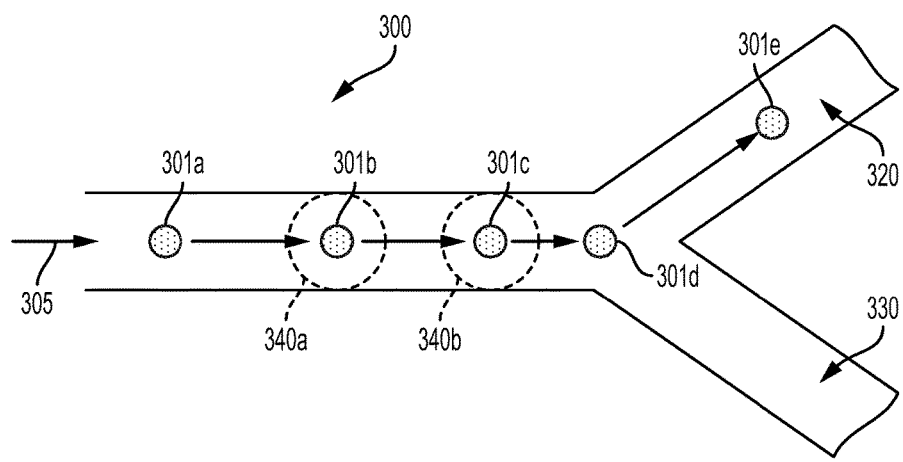
FIG. 3A illustrates an example microfluidic system.

FIG. 3A illustrates an example channel 300 (e.g., a microfluidic channel within a stage) of an imaging apparatus. A scatterer (e.g., a cell, an engineered particle, an instance of a contrast agent, a magnetic nanoparticle) is shown at several different locations 301a-e as the scatterer travels through the channel 300. The travel of the scatterer through the channel 300 could be facilitated by a flow 305 of a carrier fluid (e.g., saline, oil, blood, blood plasma) though the channel 300. The channel 300 branches into first 320 and second 330 sub-channels. The sub-channels 320, 330 are connected to respective different locations (e.g., different cuvettes or other storage means). At a first time, $T_1$, the scatterer is at a first location (illustrated as scatterer 301a) within the channel 300. The flow 305 of carrier fluid causes the scatterer to move within a first target region 340a (illustrated as scatterer 301b) at a second time, $T_2$, that encompasses a portion of the channel 300. The flow 305 of carrier fluid then causes the scatterer to move within a second target region 340b (illustrated as scatterer 301c) at a third time, $T_3$, that encompasses a further portion of the channel 300. The flow 305 of carrier fluid then causes the scatterer to move within a branching region (illustrated as scatterer 301d) of the channel at a fourth time, $T_4$. At a fifth time, $T_5$, the scatterer has moved into the first sub-channel 320 (illustrated as scatterer 301e).

Note that, while the first 340a and second 340b target regions illustrated in FIG. 3A are non-overlapping, first and second target regions of an imaging system as described herein could be partially overlapping or coextensive, according to an application. In some examples, the relative locations of such first and second target regions could be controllable (e.g., by operating an actuator of a movable stage and/or by controlling a location or direction of a beam of illumination used to illuminated the first and/or second target regions) such that whether the first and second target regions overlap and/or a degree of such overlap may be controllable.

The scatterer could be sorted into one of a number of different locations (e.g., storage locations within cuvettes or other storage means) based, e.g., on an identity or other information about the scatterer determined based on an image of the scatterer, an intensity waveform of light scattered by the scatterer, or some other information detected about the scatterer. Sorting the scatterer could include selecting one of the two sub-channels 320, 330 (e.g., based on a determined identity of the scatterer) and, based on the selection, directing the scatterer into the selected sub-channel. Such sorting could be effected by application of a force to the scatterer and/or to the carrier fluid. Exerting such a force could include controlling a microfluidic valve or other fluid control means to control relative flow rates of carrier fluid through the sub-channels 320, 330, by applying an electrical field to exert a force on a charged scatterer, by applying an electrical field or voltage to change an interfacial energy of a surface within one or both of the sub-channels 320, 330 (e.g., to repel the carrier fluid from one of the sub-channels 320, 330), by controlling a microfluidic valve or other fluid control means to control relative flow rates of carrier fluid through additional channels (not shown), or performing some other action.

Figure 3B:
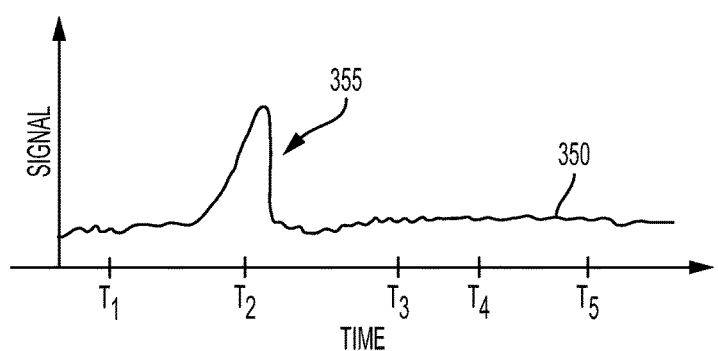
FIG. 3B illustrates an example signal generated by an example imaging apparatus.

An identity or other information about the scatterer could be determined based on an image of the scatterer, an intensity waveform of light scattered by the scatterer, or some other detected property of the scatterer. For example, the first target region 340a could be illuminated, and an intensity or other property of light scattered from the first target region 340a could be detected, e.g., by a light sensor that receives the scattered light via an immersion objective, as described elsewhere herein. FIG. 3B illustrates an example time-varying waveform 350 of the intensity of such scattered light. As the scatterer passes through the first target region 340a at time $T_2$, the intensity of the scattered light changes (e.g., exhibiting the peak 355 shown in FIG. 3B). A maximum intensity, a mean intensity, a waveform, a rise time, a rise rate, a fall time, a fall rate, or some other properties of the time-varying waveform 350 at our about time $T_2$ (e.g., of the peak 355) could be determined, based on the detected intensity of the scattered light, and used to determine a type of the scatterer (e.g., a red blood cell, a neutrophil, a magnetic nanoparticle), a size or other dimensional property of the scatterer (e.g., a diameter, a length, a characteristic dimension of a surface texture), a granularity, dimension, number, density, or other property of scattering contents of the scatterer (e.g., a density of lysosomes within a cell), or some other information about the scatterer.

The scatterer could also be imaged while present in the channel 300. For example, an image sensor could receive, via an immersion objective, in-focus light from the first target area 340a to generate an image of the scatterer at time $T_2$. Additionally or alternatively, an image sensor could receive, via an immersion objective, in-focus light from the second target area 340b to generate an image of the scatterer at time $T_3$. Such an image could be used (e.g., in combination with information about light scattered from the scatterer) to identify the scatterer and/or to determine some information about the scatterer. In some examples, imaging the scatterer could be performed based on the detected intensity of light scattered from the scatterer when the scatterer in the first target area 340a. For example, it could be determined, based on the detected intensity of the scattered light, that the scatterer is present in the first target area 340a at time $T_2$ and/or that the scatterer has a particular identity or other property. Based on that determination, the image sensor could be operated, at time $T_3$, to image in-focus light from the second target area 430b to generate an image of the scatterer. Additionally or alternatively, the scatterer could be sorted based on such determined information, e.g., sorting means could be operated at time T4 to effect movement of the scatterer into the first sub-channel 320.

Figure 4:
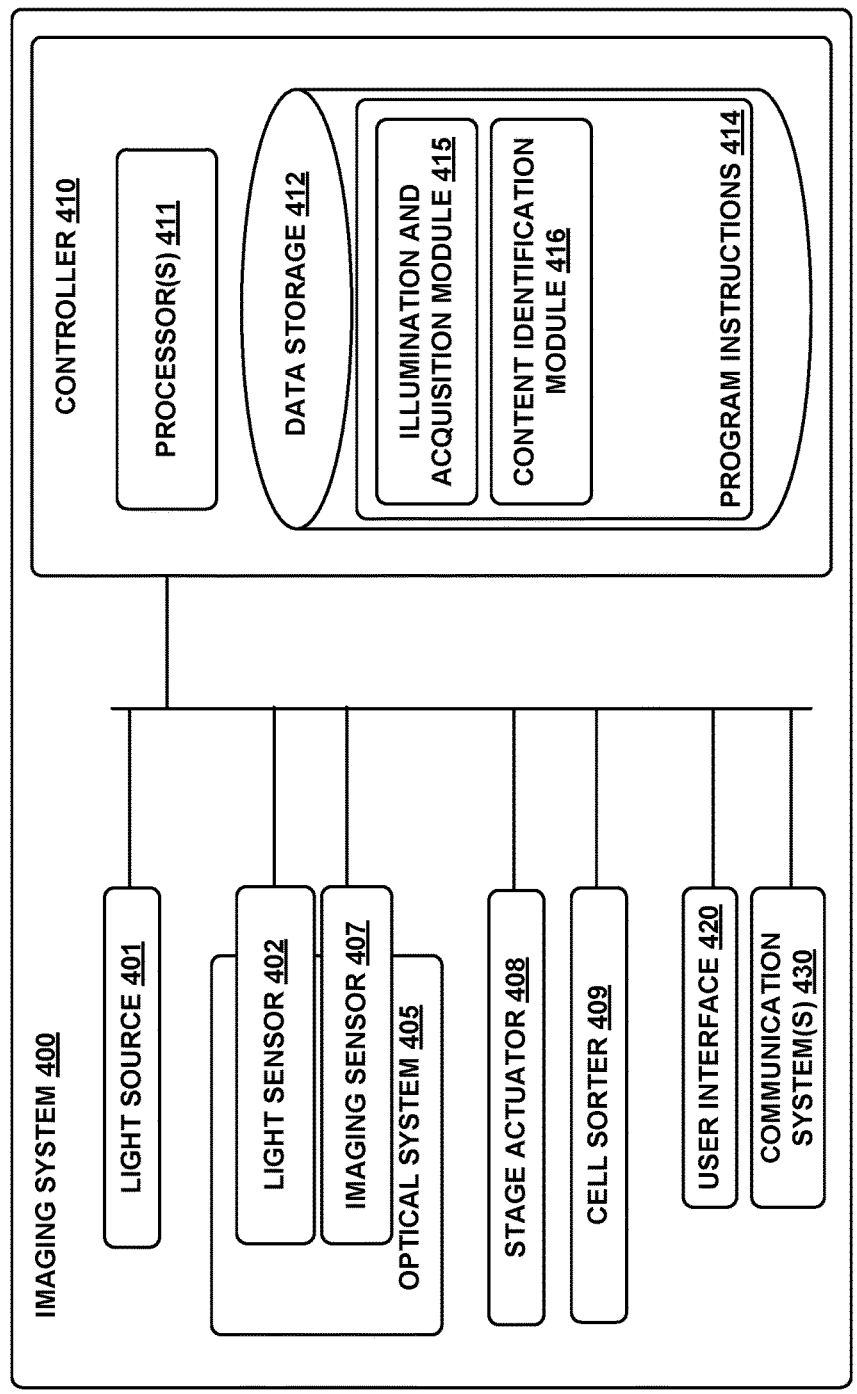
FIG. 4 is a functional block diagram of an example imaging system.

Other methods of configuring and/or operating a light source, light sensor(s), imaging sensor(s), container(s), window(s), stage(s), and/or other elements of an imaging system (e.g., to identify and/or image cells or other particles within a flowing carrier fluid or some other environment or sample of interest) are anticipated III. Example Electronics of an Imaging Apparatus FIG. 4 is a simplified block diagram illustrating the components of an imaging system 400, according to an example embodiment. Imaging system 400 and/or elements thereof may take the form of or be similar to one of the example systems or elements 100 or 200 shown in FIG. 1 or 2 or of some other systems. Imaging system 400 may take a variety of forms, such as a wall, table, ceiling, or floor-mounted device. Imaging system 400 may take the form of a bench-top or table-top device (e.g., a bench-top microscope). Imaging system 400 and/or elements thereof could also take the form of a system, device, or combination of devices that is configured to be part of another device, apparatus, or system. For example, imaging system 400 or element(s) thereof could take the form of a system or element configured to be mounted to or otherwise disposed as part of some other imaging system (e.g., container 110 and/or the light source 160 or other elements of the imaging system 100 could be configured to be part of an immersion microscope or other imaging system, e.g., to enable such a system to perform side-scatter measurements of a sample in addition to high-resolution imaging of the sample using the immersion objective). Imaging system 400 could take the form of a system configured to contents of an industrial environment, medical environment, scientific environment, or some other environment. Imaging system 400 also could take other forms.

In particular, FIG. 4 shows an example of an imaging system 400 having a light source 401, a light sensor 402, an image sensor 407, an optical system 405 that includes an immersion objective, a stage actuator 408, a cell sorter 409, a user interface 420, communication system(s) 430 for transmitting data to a remote system, and controller 410. The components of the imaging system 400 may be disposed on or within a mount or housing or on some other structure for mounting the system to enable stable imaging or other functions relative to a sample of interest, for example, a biological sample contained within a stage (e.g., a stage having a location relative to other elements of the imaging system 400 that is actuated in at least one dimension by the stage actuator 408). The imaging system 400 could include additional components, for example, a carrier fluid pump configured to provide a carrier fluid to transport cells or other scatterers of interest into and/or through one or more target regions of the imaging system 400 or some other instrument(s) or other component(s) according to an application.

The light source 401, light sensor 402, image sensor 407, optical system 405, cell sorter 409, and/or stage actuator 408 could be configured and/or disposed as part of the imaging system 400 as described elsewhere herein for similar elements. The optical system 405 is configured to optically couple the light sensor 402 to a first target area such that light emitted by the light source 401 that has been scattered by one or more scatterers present in a first target area is received, via the immersion objective, by the light sensor 402. The optical system 405 is additionally configured to optically couple the image sensor 407 to a second target area (which may fully or partially overlap with the first target area) such that the image sensor 407 receives, via the immersion objective, in-focus light from the second target area that can be used, by the image sensor 407, to generate an image of one or more scatterers or other contents of the second target area. The optical system 405 may be configured to provide additional functionality, e.g., to couple a further light source, via the immersion objective, to the first and/or second target areas such that the further light source may be operated to illuminate such target areas.

The cell sorter 409 could comprise microfluidic channels, microfluidic valves, one or more reservoirs for storage of sorted cells or other scatterers, vibrators for partitioning a carrier fluid containing scatterers into a plurality of sort-able droplets, electrodes for charging and/or exerting electrostatic forces on such droplets, electrodes for controlling a surface energy of one or more surfaces within a microfluidic circuit to control a location, a direction of flow, or some other property of carrier fluid flow within a microfluidic circuit, or some other components to facilitate sorting of cells or other scatterers optically interrogated by the imaging system.

Controller 410 may be provided as a computing device that includes one or more processors 411. The one or more processors 411 can be configured to execute computer-readable program instructions 414 that are stored in a computer readable data storage 412 and that are executable to provide the functionality of an imaging system 400 as described herein.

The computer readable data storage 412 may include or take the form of one or more non-transitory, computer-readable storage media that can be read or accessed by at least one processor 411. The one or more computer-readable storage media can include volatile and/or non-volatile storage components, such as optical, magnetic, organic or other memory or disc storage, which can be integrated in whole or in part with at least one of the one or more processors 411. In some embodiments, the computer readable data storage 412 can be implemented using a single physical device (e.g., one optical, magnetic, organic or other memory or disc storage unit), while in other embodiments, the computer readable data storage 412 can be implemented using two or more physical devices.

The program instructions 414 stored on the computer readable data storage 412 may include instructions to perform any of the methods described herein. For instance, in the illustrated embodiment, program instructions 414 include an illumination and acquisition module 415 and a content identification module 416.

The illumination and acquisition module 415 can include instructions for operating the light source 401, light sensor 402, image sensor 407, cell sorter 409, and/or stage actuator 408 to enable any of the functions or applications of an imaging system to optically interrogate, determine an identity or other properties of, sort into one or more locations, and/or otherwise image or interact with one or more scatterers as described herein. Generally, instructions in the illumination and acquisition module 415 provide methods of operating the light source 401 to illuminate a first target region that may contain one or more scatterers. Instructions in the illumination and acquisition module 415 further provide methods of operating the light sensor 402 to detect an intensity of light emitted from the light source 401 that is scattered from the first target region (e.g., by one or more scatterers located therein). Instructions in the illumination and acquisition module 415 yet further provide methods of operating the image sensor 407 to generate images of one or more scatterers or other contents of the second target region. In some examples, these instructions could include instructions for operating the imaging sensor 407 to generate an image at a determined time relative to a peak or other feature present in a time-varying light intensity detected by the light sensor 402 (e.g., a peak corresponding to the presence of one or more scatterers in the first target region). Other operations, functions, and applications of the light source 401, light sensor 402, image sensor 407, cell sorter 409, stage actuator 408, and/or of other components of the imaging system 400 as described herein could be implemented as program instructions in the illumination and detection module 415.

The content identification module 416 can include instructions for identifying, sorting into one or more locations, determining a characteristic size of, or determining some other information about one or more scatterers that have been optically interrogated by the imaging system 400. This could include determining, based on an intensity of scattered light detected by the light sensor 402, a presence, identity, size, or other information about one or more scatterers present in the first target region. Such determinations could also be based on one or more images generated of the one or more scatterers (e.g., when the one or more scatterers are present in the first and/or second target regions) by the image sensor 407. Such a determination could be used, by the illumination and acquisition module 415, to operate the cell sorter 409 to sort the one or more scatterers into one or more locations (e.g., according to the identity of each of the one or more scatterers), to operate the image sensor 405 to generate an image of the one or more scatterers (e.g., during a determined period of time when the one or more scatterers are present in the second target region), or to perform some other operation(s). In some examples, the content identification module 416 can include instructions for updating the content identification module 416 (e.g., for updating one or more parameters of a cell identification algorithm of the content identification module 416) to improve an accuracy with which cells or other scatterers may be identified based, e.g., on the intensity of scattered light detected by the light sensor 402.

Some of the program instructions of the illumination and acquisition module 415 and/or content identification module 416 may, in some examples, be stored in a computer-readable medium and executed by a processor located external to the imaging system 400. For example, the imaging system 400 could be configured to illuminate and to receive light from one or more target regions and then transmit related data to a remote server, which may include a mobile device, a personal computer, the cloud, or any other remote system, for further processing (e.g., for the identification of one or more scatterers).

User interface 420 could include indicators, displays, buttons, touchscreens, head-mounted displays, and/or other elements configured to present information about the imaging system 400 to a user and/or to allow the user to operate the imaging system 400. Additionally or alternatively, the imaging system 400 could be configured to communicate with another system (e.g., a cellphone, a tablet, a computer, a remote server) and to present elements of a user interface using the remote system. The user interface 420 could be disposed proximate to the light source 401, light sensor 402, imaging sensor 407, stage actuator 408, sell sorter 409, controller 410, or other elements of the imaging system 400 or could be disposed away from other elements of the imaging system 400 and could further be in wired or wireless communication with the other elements of the imaging system 400. The user interface 420 could be configured to allow a user to specify some operation, function, or property of operation of the imaging system 400. The user interface 420 could be configured to present an image of a sample (e.g., an image of a cell or other contents of the sample) generated by the imaging system 400 or to present some other information to a user (e.g., a distribution of identified cells in a sample). Other configurations and methods of operation of a user interface 420 are anticipated.

Communication system(s) 430 may also be operated by instructions within the program instructions 414, such as instructions for sending and/or receiving information via a wireless antenna, which may be disposed on or in the imaging system 400. The communication system(s) 430 can optionally include one or more oscillators, mixers, frequency injectors, etc. to modulate and/or demodulate information on a carrier frequency to be transmitted and/or received by the antenna. In some examples, the imaging system 400 is configured to indicate an output from the controller 410 (e.g., one or more images of a target) by transmitting an electromagnetic or other wireless signal according to one or more wireless communications standards (e.g., Bluetooth, WiFi, IrDA, ZigBee, WiMAX, LTE). In some examples, the communication system(s) 430 could include one or more wired communications interfaces and the imaging system 400 could be configured to indicate an output from the controller 410 by operating the one or more wired communications interfaces according to one or more wired communications standards (e.g., USB, FireWire, Ethernet, RS-232).

The computer readable data storage 412 may further contain other data or information, such as contain calibration data corresponding to a configuration of the imaging system 400, properties of a calibration fluid or sample, or some other information. Calibration, imaging, and/or other data may also be generated by a remote server and transmitted to the imaging system 400 via communication system(s) 430.

IV. Example Methods

Figure 5:
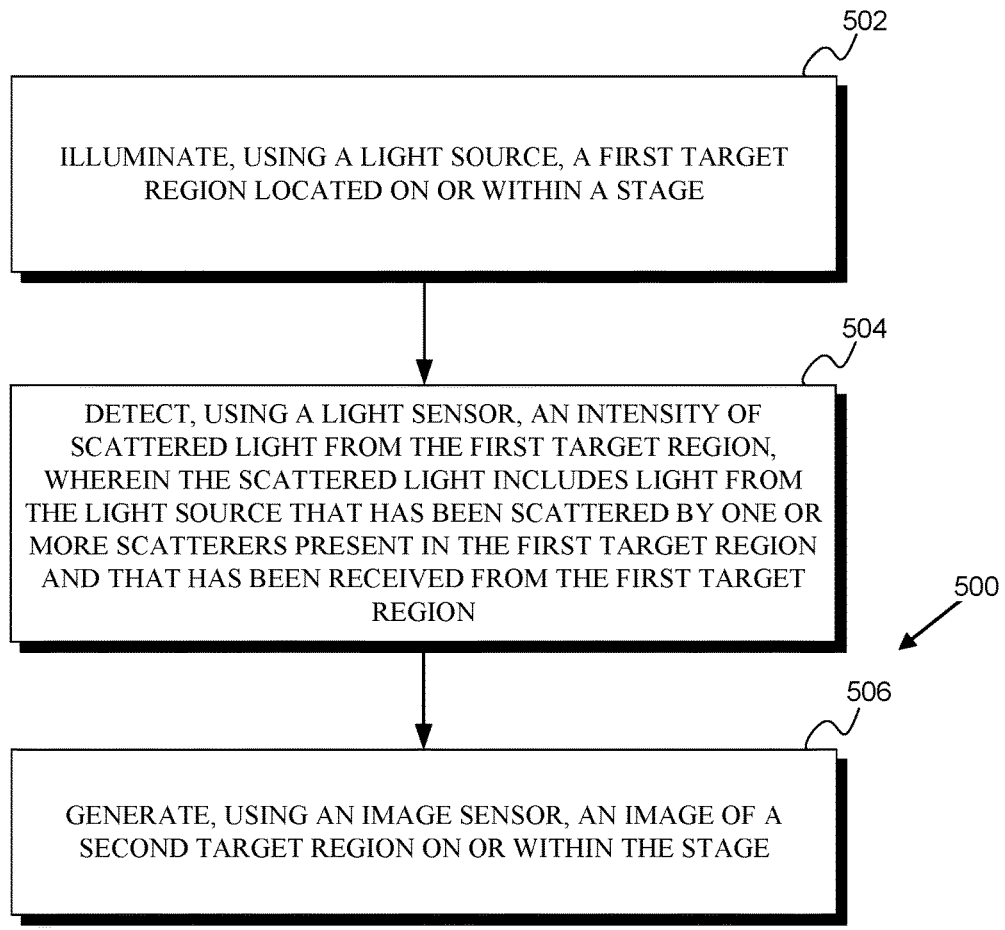
FIG. 5 is a flowchart of an example method.

FIG. 5 is a flowchart of an example method 500 for operating elements of an imaging system to image, using an immersion objective, a sample and to detect an intensity or other property of side-scattered light from the sample via the immersion objective. The imaging system includes (i) a stage; (ii) the immersion objective; (iii) a container disposed on the stage; (iv) a light source; (v) a light sensor; and (vi) an image sensor. The container includes an optical window and is shaped to hold a volume of an immersion fluid such that the immersion fluid is in contact with the immersion objective, the stage, and an internal surface of the optical window. The light source is optically coupled to a first target region located on or within the stage via the optical window of the container. The light sensor is optically coupled to the first target region via the immersion objective and receives scattered light from the first target region. The image sensor is optically coupled to a second target region located on or within the stage via the immersion objective and receives in-focus light from the second target region. The imaging system could take the form of one of the imaging systems 100, 200 depicted in FIGS. 1, 2 or could take some other form as described herein.

The method 500 includes illuminating, using the light source, the first target region located on or within the stage (502). This could include illuminating the target region during one or more specified periods of time, e.g., during each of a plurality of exposure times. Using the light source to illuminate the first target region could include emitting illumination at one or more specified wavelengths, e.g., by controlling a wavelength of a tunable laser of the light source, by operating a light-emitting element (e.g., a laser, an LED) of the light source corresponding to the specified wavelength(s), or by some other method. Using the light source to illuminate the first target region could include operating one or more actuated mirrors, gimbals, servomotors, or other actuators to control a location and/or orientation of a beam of illumination emitted from the light source, e.g., based on images of fiducials or other registration features formed or disposed on the container, based on images of the first target region taken using the image sensor, based on an intensity of light detected using the light source, or based on some other information.

The method 500 further includes detecting, using the light sensor, an intensity of scattered light from the first target region, wherein the scattered light includes light from the light source that has been scattered by one or more scatterers present in the first target region and that has been received from the first target region (504). This could include detecting a number of photons received by the light sensor (e.g., using a photomultiplier tube, avalanche diode, or other sensing element(s)), generating an analog signal related to the intensity of the received light and sampling the generated analog signal at a plurality of points in time, filtering such an analog signal before such sampling, or detecting the intensity of the scattered light according to some other method and/or using some other apparatus. In some examples, detecting an intensity of scattered light from the first target region could include detecting an intensity of light received by the light sensor during one or more periods of time when the light source is emitting illumination (e.g., during a plurality of exposure times). In some examples, detecting an intensity of scattered light from the first target region could include detecting an intensity of light at one or more specified wavelengths that is received by the light sensor, e.g., using a dichroic mirror or other optical filter to detect an intensity of light at a wavelength corresponding to a wavelength of light emitted by the light source.

The method 500 further includes generating, using the image sensor, an image of a second target region on or within the stage (506). This could include operating a CCD, an array of CMOS light sensors, or some other means for generating an image. Using the image sensor to generate an image of a second target region could include generating a plurality of images during respective periods of time (e.g., respective exposure times). Such periods of time could correspond to periods of time when the second target region is being illuminated (e.g., by the light source, by some other source of illumination). Using the image sensor to generate an image of a second target region could include operating a servomotor, a piezo actuator, an electrowetting lens, an actuated diffraction grating, or some other optical elements to control a location of the second target region (e.g., relative to the immersion objective, by moving the stage relative to the immersion objective), to control a focal distance or length of the immersion objective, or to control some other element(s) of an optical system via which light travels from the second target region to arrive, in-focus, at the image sensor. In some examples, the second target region could wholly or partially overlap the first target region (e.g., the image sensor could operate to generate an image of one or more scatterers in the first target region). Using the image sensor to generate an image could be performed in response to a detected or determined property of the intensity detected using the light sensor, e.g., the detected intensity could be used to identify a cell or other scatterer(s) present in the first target region and, responsive to such a determination, the image sensor could be operated to generate an image (e.g., of the identified cell or other scatterer).

The method 500 could include other additional steps or elements. The method could include identifying a cell or other scatterer(s) present in the first and/or second target regions (e.g., based on the detected intensity and/or one or more generated images). Such identification could include determining a type of the cell or other scatterer (e.g., a red blood cell, a neutrophil, a magnetic nanoparticle), determining a size or other dimensional property of the cell or other scatterer (e.g., a diameter, a length, a characteristic dimension of a surface texture), determining a granularity, dimension, number, density, or other property of scattering contents of the cell or other scatterer (e.g., a density of lysosomes within a cell), or determining some other identifying information about the cell or other scatterer(s) in the first or second target regions. The method 500 could include performing some operations based on such identification, e.g., operating electrodes, a microfluidic component, or some other apparatus to sort the identified cell(s) or other scatterer(s) into one or more locations (e.g., respective different microfluidic channels, cuvettes, or other storage means). The method 500 could include illuminating one or both of the first or second target locations, e.g., via the immersion objective. The method 500 could include detecting the intensity of further portions of light scattered by, transmitted through, or otherwise interacted with by the cell or other scatterer(s) within the first target region. The method 500 could include any additional steps, or could include details of implementation of the listed steps 501, 504, 506 or of other additional steps, as described herein in relation to the operation of an imaging system. Additional and alternative steps of the method 500 are anticipated.

V. Conclusion

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to image biological environments (e.g., cell samples extracted from a human body) and to image and/or otherwise determine information about cells within such environments, it is noted that the disclosed devices, systems, and methods can be applied in other contexts as well. For example, imaging systems configured as disclosed herein may be included as part of other scientific and/or industrial imaging apparatus.

Additionally, while various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
    a stage;
    an immersion objective;
    a container disposed on the stage, wherein the container comprises an optical window, and wherein the container is shaped to hold a volume of an immersion fluid such that the immersion fluid is in contact with the immersion objective, the stage, and an internal surface of the optical window;
    a light source, wherein the light source is optically coupled to a first target region located on or within the stage via the optical window of the container;
    a light sensor, wherein the light sensor is optically coupled to the first target region via the immersion objective, wherein the light sensor receives scattered light from the first target region, wherein the scattered light comprises light from the light source that has been scattered by one or more scatterers present in the first target region;
    an image sensor, wherein the image sensor is optically coupled to a second target region located on or within the stage via the immersion objective such that the image sensor receives image light in-focus from the second target region; and
    a controller that is operably coupled to the light sensor and that is operable to perform controller operations comprising:
        detecting an intensity of the scattered light received by the light sensor;
        identifying, based on the detected intensity, the one or more scatterers; and
        sorting the one or more scatterers into one or more locations based on the determined identity of the one or more scatterers.

2. The system of claim 1, wherein the stage comprises a transparent layer and a microfluidic layer disposed on the transparent layer, wherein the microfluidic layer comprises a channel, and wherein the first target region comprises a portion of the channel.

3. The system of claim 2, wherein the microfluidic layer is removably mounted to the transparent layer.

4. The system of claim 1, wherein the optical window comprises an anti-reflective coating.

5. The system of claim 1, wherein the optical window comprises a material having a refractive index that matches a refractive index of the immersion fluid.

6. The system of claim 1, further comprising a further light sensor, wherein the further light sensor receives light from the light source transmitted through the first target region.

7. The system of claim 1, further comprising a dichroic mirror, wherein the light source emits light at a first wavelength and the in-focus light comprises light at a second wavelength, wherein the dichroic mirror reflects the light at the first wavelength and transmits the light at the second wavelength, wherein the image sensor receives the light at the second wavelength via transmission through the dichroic mirror, and wherein the light sensor receives the light at the first wavelength via reflection from the dichroic mirror.

8. The system of claim 1, wherein the first target region and the second target region at least partially overlap.

9. The system of claim 8, further comprising a controller that is operably coupled to the light sensor and the image sensor, wherein the controller is operable to perform controller operations comprising:
  detecting an intensity of scattered light received by the light sensor;
  identifying, based on the detected intensity, the one or more scatterers; and
  responsive to identifying the one or more scatterers, using the image sensor to generate an image of the one or more scatterers.

10. The system of claim 1, further comprising a further light source, wherein the further light source is optically coupled to the second target region via the immersion objective, and wherein the in-focus light received by the image sensor comprises light emitted from the second target region due to illumination of the second target region by the further light source.

11. The system of claim 1, wherein the stage is movable relative to the immersion objective.

12. The system of claim 1, wherein the light source emits a beam of illumination to illuminate the first target region via the optical window of the container, and wherein the light source is configured such that at least one of a location or an orientation of the emitted beam of illumination is adjustable.

13. A method comprising:
  illuminating, using a light source, a first target region located on or within a stage, wherein a container is disposed on the stage, wherein the container comprises an optical window, wherein the container contains a volume of immersion fluid such that the contained volume of immersion fluid is in contact with an immersion objective, the stage, and an internal surface of the optical window, and wherein illuminating the first target region comprises using the light source to provide illumination to the first target region via the optical window of the container;
  detecting, using a light sensor, an intensity of scattered light from the first target region, wherein the scattered light comprises light from the light source that has been scattered by one or more scatterers present in the first target region, wherein the light sensor receives the scattered light from the first target region via the immersion objective;
  generating, using an image sensor, an image of a second target region on or within the stage, wherein the image sensor is optically coupled to the second target region via the immersion objective such that the image sensor receives image light in-focus from the second target region;
  identifying, based on the detected intensity, the one or more scatterers; and
  sorting the one or more scatterers into one or more locations based on the determined identity of the one or more scatterers.

14. The method of claim 13, wherein the stage comprises a transparent layer and a microfluidic layer disposed on the transparent layer, wherein the microfluidic layer comprises a channel, wherein the first target region comprises a portion of the channel.

15. The method of claim 14, further comprising:
  wherein the in-focus light received by the image sensor is emitted from the one or more scatterers, and wherein identifying the one or more scatterers comprises identifying the one or more scatterers based on the image generated using the image sensor.

16. The method of claim 13, wherein the in-focus light received by the image sensor is emitted from the one or more scatterers, and wherein the method further comprises:
  identifying, based on the detected intensity, the one or more scatterers, wherein using the image sensor to generate an image is performed responsive to identifying the one or more scatterers.

17. The method of claim 13, further comprising:
  illuminating, using a further light source, the second target region, wherein the further light source is optically coupled to the second target region via the immersion objective.

* * * * *